United States Patent [19]
Taheri et al.

[11] Patent Number: 5,591,195
[45] Date of Patent: Jan. 7, 1997

[54] APPARATUS AND METHOD FOR ENGRAFTING A BLOOD VESSEL

[76] Inventors: Syde Taheri, 268 Dan Troy, Williamsville, N.Y. 14221; Howard J. Leonhardt, 13794 NW. 4th St., Bldg. #210, Sunrise, Fla. 33325

[21] Appl. No.: 549,880

[22] Filed: Oct. 30, 1995

[51] Int. Cl.⁶ .................................................. A61M 29/00
[52] U.S. Cl. ........................ 606/194; 606/198; 606/191; 623/1; 623/12
[58] Field of Search .................................. 606/192, 193, 606/194, 195, 197, 198; 623/1, 12; 604/96, 104

[56] References Cited

U.S. PATENT DOCUMENTS

| | | | |
|---|---|---|---|
| 4,580,568 | 4/1986 | Gianturco | 623/1 |
| 4,878,906 | 11/1989 | Lindemann et al. | 623/1 |
| 5,236,447 | 8/1993 | Kubo et al. | 623/1 |
| 5,507,771 | 4/1996 | Gianturco | 623/1 |

OTHER PUBLICATIONS

The Dotter, Buschmann, McKinney and Bosch article technial Development and Instrumentation Dec. 7, 1982 Oregon Health Sciences University Dept. of Diagnostics Radiology.

Parodi, MD, Palmaz MD, and Barone PhD University of Texas.

*Primary Examiner*—Michael Powell Buiz
*Assistant Examiner*—Kevin Truong
*Attorney, Agent, or Firm*—The Law Offices of Byron A. Bilicki, P.C.

[57] ABSTRACT

A method and apparatus for engrafting a blood vessel is disclosed. The apparatus includes a hollow tubular graft of a preselected cross section having a proximal and distal end containing compressable and expandable nitinol springs, and connecting bars to facilitate physical communication between both springs. Furthermore, the apparatus contains a transport and deployment member for delivering said hollow tublar graft to an engrafting site within a blood vessel. The transport and deployment apparatus is comprised of an insertion catheter having a graft balloon and a tip balloon, as well as multiple inner tracks for injection of fluid into said balloons and the blood vessel interior. The method includes transport and deployment of said graft, as well as non surgical movement and removal of said graft in the event of misplacement.

14 Claims, 9 Drawing Sheets

TALENT Balloon Catheter Vessel Mapping System

| Syringe Plunger Position - Volume Fluid Infused | Balloon Diameter | Pressure on Gauge | Vessel Diameter and Strength |
|---|---|---|---|
| 5ccs | 7.5mms | 0 | 7.5mms Unkown |
| 10ccs | 15mms | 0 | 15mms Unkown |
| 15ccs | 22.5mms | 0 | 22.5mms Unkown |
| 18ccs | 27mms | 1psi | 27mms Unkown |
| 20ccs | 30mms | 5psi | 30mms Unkown |
| 18ccs | 27mms | 3psi | 27mms Strong Wall |
| 15ccs | 22.5mms | 2psi | 22.5mms Strong Wall |

*FIG. 9*

Table of Vessel Size to Spring Size to Graft Size Relationship

| Vessel Size | Middle Portion Graft Size | Expanded End Portions Size | Pre-embedded Nitinol Spring Size | Introducer Size |
|---|---|---|---|---|
| 10mms | 10mms | 14mms | 14mms | 14FR |
| 14mms | 14mms | 20mms | 20mms | 14FR |
| 16mms | 16mms | 22mms | 22mms | 14FR |
| 18mms | 18mms | 24mms | 24mms | 16FR |
| 20mms | 20mms | 28mms | 28mms | 16FR |
| 22mms | 22mms | 30mms | 30mms | 16FR |
| 24mms | 24mms | 32mms | 32mms | 18FR |
| 26mms | 26mms | 36mms | 36mms | 18FR |
| 28mms | 28mms | 38mms | 38mms | 18FR |
| 30mms | 30mms | 40mms | 40mms | 18FR |

*FIG. 10*

APPARATUS AND METHOD FOR ENGRAFTING A BLOOD VESSEL

BACKGROUND OF THE INVENTION

1. Field

The present invention relates to medical prostheses and to a method and apparatus for performing aneurysm repair, and more particularly to a method and apparatus for performing aneurysm repair by placing a graft percutaneously via an insertion catheter having a controllable inflatable balloon disposed about and integral with its distal end.

2. Prior Art

Aortic aneurysms, or ruptures, are a very common type deteriorating disease which tend to affect blood vessels. Aneurysms often affect the ability of the lumen to conduct fluids and in turn may at times be life threatening. The standard treatment for aneurysms is to surgically remove the aneurysm and graft a replacement prosthetic section into the lumen. However, such surgery is generally postponed until the aneurysm has grown to a diameter greater than five cm. With aneurysms over five cm in diameter, the risk of complications is greater than the risks inherent in surgical excision and grafting of the aneurysm. Consequently, aortic aneurysms, or those that show a rapid increase in size, or those greater than five cm in diameter are generally surgically removed and grafted as a matter of course, before rupture occurs.

The typical procedure for repairing an aortic aneurysm requires one or two days of preparing the large and small intestines prior to hospitalization. The operation itself will generally take one to three hours, and necessitate several units of blood transfusion. The patient commonly remains hospitalized for several days following surgery, and requires as much as three months recuperation time before returning to work. Even for surgical excision and grafting of an aneurysm, there remains significantly high rates of mortality and morbidity. The mortality rate is as high as eight percent (8%). The morbidity rate includes incident complications such as blood loss, respiratory tract infections, wound infections, graft infections, renal failure, and ischemia of the bleeding intestine. The mortality and morbidity rates for this type of major surgery are also often influenced by the fact that the typical aortic aneurysm patient is elderly and therefore less able to withstand major surgery and a major anesthesia.

Another surgical procedure for repairing an aneurysm is to excise part or all of the aneurysm and replace the aneurysmal lumen section with a man made tubular section, sutured end-to-end to the severed lumen at a site proximal to the origination of the aneurysm.

Other methods of repairing aneurysms involve placing graft within the vascular system via catheters through the femoral artery. Conventional tubular aortic replacement sections, however, are generally considerably larger in diameter than the femoral artery and therefore cannot be inserted through the femoral artery lumen. Also, where such devices have been proposed, as in, for example, the devices of U.S. Pat. Nos. 4,140,126 and 4,562,596 by Choudhury and Kornberg, respectively, the expanding structure of the devices are cumbersome, and difficult to operate.

U.S. Pat. No. 5,104,399, to Lazarus discloses an artificial graft and implantation method. Graft is of a preselected cross section and length and is capable of being substantially deformed so as to accommodate the interior surface of the blood vessel as well as stapling means for securing it to the blood vessel. The system further includes a capsule for delivering graft, thereby overcoming some of the complications of the prior art.

The majority of other grafting systems, such as U.S. Pat. Nos. 5,304,220 to Maginot and 5,151,105 to Kwan-Gett, employ a variety of insertion means, but they require additional suturing or other methods for securing graft. Furthermore, once a graft has been placed inside the lumen, adjustment usually requires a major surgical procedure. The difficulties involved with traditional surgical procedures and additional complexities associated with securing grafts make the treatment of aneurysms a very expensive and lengthy procedure.

Thus, there exists a need for a treatment for aneurysms which requires minimal preparation and outpatient care while providing a safe and percutaneous method for implanting grafts which do not require additional suturing or stapling for security.

SUMMARY OF THE INVENTION

The present invention relates to a method and apparatus for performing rupture sizing and repair. The system is characterized by a graft which can be placed percutaneously via an insertion catheter having two controllable, inflatable and deflatable balloons, as well as a plurality of interior tracks for utilizing a kink resistant nitinol core wire, a guide wire, and a condensing spring push rod to provide enhanced pushability and support, and for fluid injection into the balloons and the lumen of the blood vessel. Such placement is facilitated by a standard sheath introducer which is equipped with a hemostasis valve to prevent leakage of blood from the system. The sheath introducer may further include a side port and may be as small as 14FR. The graft is comprised of at least two nitinol springs which are embedded in graft material at each end and covered completely by the material so as to prevent direct exposure to bodily fluids or tissue. Furthermore, the graft contains a nitinol wire mesh extension to allow bedside sizing with standard operating room scissors. Nitinol connecting bars are laser welded to the nitinol springs, or crimped fit with nitinol or steel hypodermic tubing in order to place the springs in physical communication with each other, inhibit twisting or bunching of graft material, and secure fixation of the graft to the blood vessel wall. The nitinol connecting bars also provide extra security during deployment and positioning of graft.

Nitinol is a biologically inert alloy which possesses special shape-memory properties. The alloy consists of roughly equal portions of nickel and titanium. The shape-memory properties of nitinol allow a wire coil spring which is initially fabricated with a desired shape and configuration to be reshaped into a temporary compressed configuration, which is more suitable for transluminal placement. The alloy composed is typically stable at room and body temperature, but can be forced to lose its malleability and permanently revert to its initially fabricated configuration. This thermally induced reversion occurs due to a crystalline transition from the martensitic to austenitic phase. The transition temperature of the alloy can be controlled by varying its composition and processing.

Prior to the selection and placement of a graft, the ruptured blood vessel must be sized. The method for sizing the diameter of a blood vessel and length of an rupture to determine the necessary size of a graft involves, generally, the use of a controllable, inflatable and deflatable balloon sizing catheter. The sizing catheter is generally comprised of an embedded kink resistant nitinol core wire and four (4) lumens, one for the condensing spring push rod; one for injection of fluid into the sizing balloon for sizing balloon inflation, preferably contrast media to enhance visual communication; one for injection of fluid into the tip balloon for the balloon inflation, and one for the guide wire and injection of fluid, again, preferably contrast media, into the lumen of a blood vessel to enhance visual communication. A syringe is the preferred means for injection of the fluid into the balloons of the sizing catheter as well as into the lumen of a blood vessel. The syringe is equipped with a means for measuring the amount of fluid injected, such as measuring lines, as well as a pressure gauge to track resistance to sizing balloon inflation. The pressure gauge will react when the balloon expands to the size of the diameter of the lumen of the blood vessel and thereby makes contact with the blood vessel wall. Such contact creates a sudden increase in resistance to the injection of contrast media, or other fluid, into the balloon. When the balloon makes such contact with the blood vessel wall, the pressure gauge indicates a significant increase in pressure by sudden deflection, associated with injection of the fluid into the balloon. The sudden increase in pressure will be an indication to the operator that the balloon is of a size consistent with the diameter of the blood vessel, and measurement of the diameter of the blood vessel is then based upon the amount of fluid injected into the balloon. The measurement will then dictate the selection of size of the diameter of graft at full expansion.

The current apparatus allows placement of the graft through a smaller entry puncture than the prior art allows. The distal end of an insertion catheter (the distal end is the end farthest from the point of entry into the human body, and not the end farthest from the heart) is placed within the lumen of the graft with its tip balloon extending beyond the distal end of the graft, then the graft is compressed and pre-loaded with the insertion catheter within a standard teflon sheath introducer. The sheath, graft, and insertion catheter are then introduced percutaneously into a blood vessel, such as the femoral artery of the patient and directed to the site of the aneurysm, such as an aortic aneurysm, using fluoroscopy.

During movement of the graft through the blood vessel the vessel is dilated by a balloon tip at the distal end of the insertion catheter. Once inserted and placed appropriately at the rupture site, the sheath which is disposed tightly about the graft is slowly and firmly pulled back across the length of graft toward the point of entry by the operator, thus releasing the graft and leaving the graft deployed in the lumen of the blood vessel. The operator must exert some inward force to the insertion catheter and condensing spring push rod while pulling the sheath back toward the point of entry so as to support the release of graft. Without such force, the sheath may not release the graft.

The pre-loaded insertion catheter, partially disposed within graft, contains an inflatable and deflatable balloon at the tip of its distal end, the tip balloon, and a second inflatable and deflatable balloon near its distal end, the graft balloon. When pre-loaded within graft, the distal nitinol spring is directly disposed about the graft balloon of the insertion catheter. At the same time the sheath is pulled back toward the point of entry, the distal nitinol spring of graft is caused to be released from the sheath and expand in the blood vessel. Inflation of the graft balloon near the distal end of the insertion catheter as the sheath is being pulled back and the distal nitinol spring is released supports the release of the graft and stabilizes graft while the sheath is being removed from its position about the graft. The graft is further stabilized by the constant force exerted by the nitinol springs against interior wall of the blood vessel. Such constant force, approximately 340 grams, exerted the top portion of each spring also prevents blood from flowing between the springs and the inner wall of the blood vessel. Furthermore, inflation of the balloon during deployment of the distal end of the insertion catheter assures several things; provides even deployment of graft material; and reduces the risk of vessel rupture from the catheter tip itself while the tip balloon is in its deflated position. Moreover, once the distal nitinol spring has been deployed, inflation of the graft balloon of the insertion catheter in the center of the distal nitinol spring provides extra strength to the friction fit of the nitinol spring against the blood vessel wall.

The graft balloon of the insertion catheter may also be used to determine whether or not the nitinol spring is against a strong portion of the blood vessel wall. Moreover, the additional force provided by the graft balloon upon the distal nitinol spring ensures that the distal nitinol spring will not move from its original position while the sheath is moved back toward the point of entry during the release of the proximal nitinol spring. Additionally, by maintaining the balloon in the inflated position during placement, the operator can prevent blood flow through the blood vessel and therefore, prevent blood flow through the open distal end of the graft which may disrupt placement.

The proximal nitinol spring is released in a manner similar to that for releasing the distal nitinol spring; that is by pulling the sheath introducer back toward the point of entry while the graft balloon of the insertion catheter is inflated and inward force is exerted upon the graft by pushing the condensing spring push rod and the insertion catheter.

If for any reason the graft is mispositioned after its deployment, the Taheri string system may be used to partially collapse the nitinol springs and reposition the graft. Once both nitinol springs have been released and proper placement of graft has been verified, the graft may be permanently secured by means of an intravascular stapling system such as the one described in U.S. Pat. No. 4,872,874 to Taheri. It should be noted that use of the stapling system need not be immediate and is in many cases optional. Such use, however, is appropriate when the patient is lacking strong vessel wall segments, to prevent further expansion of the rupture or aneurysm along the length of the blood vessel, or to provide extra security to prevent blood from flowing between the exterior of the graft and interior of the blood vessel wall. Such blood flow may upset graft placement.

Once the graft is in place, the graft balloon may be slowly deflated in order to gently introduce blood flow through graft to avoid a sudden rush of blood which is capable of moving the position of the deployed graft. The balloon may also be partially deflated after both springs have been released, then dragged through the length of the graft in order fully un-ravel and open the graft and further to remove any wrinkles and twists. The sheath and catheter can then be safely removed; and the arterial and skin incisions may be closed.

As mentioned above, the present invention further comprises a method for partially collapsing the nitinol springs after placement of the graft for movement of the graft within the blood vessel or for removal of the graft from the blood vessel. Such movement must be effected prior to implementation of stapling procedures. Such collapsing of the graft is facilitated by the looping of one or more strings around the V-portions of the proximal spring, or the proximal and distal springs, during pre-loading of the graft within the sheath introducer. The strings must be of a length sufficient to reach from the graft at the rupture site to the exterior of the body through the blood vessel for manipulation by the operator. Furthermore, the strings must be of a sufficient strength to withstand the pulling force during the collapsing of the spring(s). After placement of the graft, if it is determined that the graft must be moved or removed from the blood vessel, the operator may merely pull both ends of each string until the proximal or proximal and distal springs have collapsed, then pull the graft through the lumen of the blood vessel. If placement is secure after movement or without movement, the operator may merely pull one side of each string to remove the strings completely from the graft and blood vessel.

The present invention further provides an additional means for stopping or slowing the blood flow during placement of the graft so as to prevent misplacement of the graft due to such blood flow. The additional means comprises either a separate double balloon blocking catheter containing two inflatable and deflatable balloons or two separate single balloon blocking catheters, each containing one inflatable and deflatable balloon.

The separate double balloon blocking catheter is inserted into the jugular vein or another vein leading to the superior vena cava, then passed through the superior vena cava, into the inferior vena cava, until the two balloons are positioned, when inflated, so as to fully or partially block the superior and inferior vena cava points of entry to the right atrium and, therefore, reduce or prevent blood from flowing into the heart and throughout the body.

The separate single balloon blocking catheters are inserted simultaneously into the inferior and superior vena cava, and positioned, again, to enable inflation of the catheter balloons for stoppage or slowing of blood flow into the right atrium.

Blood flow may be slowed or stopped during placement of the graft. The catheter balloons may then be deflated slowly after the graft placement so as to gently re-introduce blood flow to the area of the graft. This means may be utilized alone or in conjunction with the balloon of the insertion catheter for such gentle re-introduction of blood flow.

After placement of the graft, the graft position may be strengthened by utilizing a tissue adhesive substance which may be applied to the exterior of the graft material prior to placement thereof. Small packets containing such tissue adhesive substance may be comprised partially of a biologically insert material such as corn starch which will dissolve over time, preferably after three days, thus providing a time release. The tissue adhesive substance contained therein is preferably Isobutyl 2 cyanoacrylate.

The invention further comprises a method and apparatus engrafting bifurcated blood vessels without multiple points of entry. The present invention contains many features which are not taught in the prior art. For example, the present invention is the only current system which may be easily repositioned or removed after the initial deployment. The present system also provides a very low entry profile of less than 14FR, thus two the grafts at 13FR would still be lower in profile than a typical 26FR to 28FR single the graft of the prior art. The present system also provides a method for sizing the blood vessel diameter and obtaining information necessary for accurate selection of the appropriate the graft size for blood vessel rupture repair. Furthermore the present invention provides an insertion catheter with superior pushability and a controllable inflatable and deflatable balloon to assure even displacement and less risk of the graft and vessel damage, as well as a controllable inflatable and deflatable tip balloon to lead the graft through a blood vessel and provoke advanced dilation thereof. Moreover, it provides a nitinol spring system which does not lock in place, but rather continuously presses against the vessel wall with a force of between 240 and 340 grams in order to hold the graft in place while conforming to the shape and size of the blood vessel and prevent blood flow between the graft and the interior wall of the blood vessel. The nitinol springs also flex so as not to create any erosion of the vessel wall at the mounting sites. Additionally, it provides connecting bars to support the graft and substantially decrease the likelihood of twisting and bunching of the graft material. Moreover, the graft material completely covers the springs and connecting bars to prevent nitinol contact with blood or tissue. Additionally, the end portions of the graft are comprised of material arranged on the springs with the web portions cut away in such a way to allow for expandability of the springs to a diameter in excess of the middle portion of the graft for enhanced flexibility in sizing.

The present invention is further distinguished from the prior art by the tissue adhesive substance applied to the graft material exterior and by utilizing the Taheri means for slowing or stopping blood flow during placement of the graft.

The present invention is further distinguished from the prior art by its ability to provide engrafting of bifurcated blood vessels with one point of entry and therefore on incision.

OBJECTS OF THE INVENTION

It is therefore an object of this invention to provide an improved method for implanting the graft prostheses in patients.

It is another object of this invention to provide a method of implanting the graft prostheses which is less invasive than traditional surgical methods.

It is yet another object of this invention to provide a method of implanting the graft prostheses having a low mortality and morbidity risk to patients.

It is yet another object of this invention to provide a method of implanting the graft prostheses which provides less hospital and outpatient care than that of normal surgical grafting procedures.

It is yet another object of this invention to provide a graft prostheses capable of being inserted with minimal incision.

It is yet another object of this invention to provide a method for sizing the blood vessel diameter.

It is yet another object of this invention to provide an improved spring assembly.

It is yet another object of this invention to provide a spring assembly which is flexible and yet capable of retaining its shape and not collapsing or folding.

It is yet another object of this invention to provide a graft prostheses capable of being secured without the use of staples or sutures.

It is yet another object of this invention to provide a graft prostheses capable of being easily removed or adjusted after being implanted.

It is yet another object of this invention to provide a method and apparatus for engrafting a bifurcated blood vessel with on incision.

It is yet another object of this invention to provide multiple means for slowing or stopping blood flow during placement of a graft.

BRIEF DESCRIPTION OF THE DRAWINGS

FIG. 9 is a chart demonstrating the relationship between volume of fluid injected into the sizing balloon and the diameter of the blood vessel.

FIG. 10 is a chart demonstrating the sizing of a graft based upon the size of the blood vessel diameter.

DETAILED DESCRIPTION OF THE PREFERRED EMBODIMENTS

Figure 1:
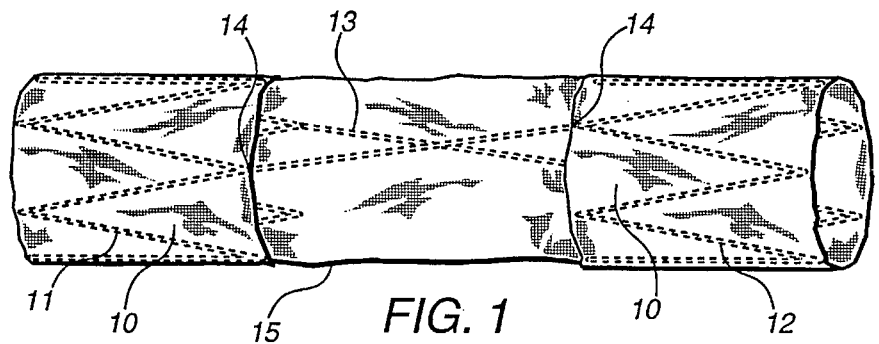
FIG. 1 is a side elevational view of a graft with a view of two nitinol springs and connecting bars, with nitinol mesh extensions connected to each spring.

For the purposes of promoting an understanding of the principles of the invention, reference will now be made to the embodiments and methods illustrated in the drawings and specific language will be used to describe the same. It will nevertheless be understood that no limitation of the scope of the invention is thereby intended; such alterations and further modifications in the illustrated devices and methods, and such further applications of the principles of the invention as illustrated therein being contemplated as would normally occur to one skilled in the art to which the invention relates.

As shown in FIG. 1 graft 15 is comprised of an expandable material 10, particularly for both end portions, preferably Dacron® or Gortex®, two nitinol springs 11, 12 embedded in proximal 11 and distal 12 ends of material 10 to provide continuous pressure to a blood vessel wall, between 240 and 340 grams of outward pushing force, and simultaneously conform to the specific diameter of a blood vessel.

As shown in FIG. 1 a graft 15 is further comprised of nitinol mesh extensions 11a, 12a extending outward in a cylindrical shape from each nitinol spring 11, 12. The nitinol mesh extensions 11a, 12a provide approximately 30 grams of outward pushing force, and enable sizing flexibility by allowing for the cutting away of portions of the nitinol mesh extensions 11a, 12a with ordinary scissors. The nitinol mesh is preferably covered with Dacron or PTFE. Preferably, material 10 completely covers both nitinol springs 11, 12 and nitinol mesh extensions, thereby preventing direct contact between the nitinol and the blood or tissue.

As shown further in FIG. 1 distal 12 and proximal 11 nitinol springs are connected by connecting bars 13. The material 10 provides complete coverage of connecting bars 13 as well, thereby, again, preventing direct contact between the nitinol and the bodily fluids or tissue. Connecting bars 13 are preferably crimped fit with steel or nitinol hypodermic tubing or laser welded to each of the inner portions 14 of proximal 11 and distal 12 nitinol springs to inhibit the twisting or bunching of graft material 10. For example, without the connecting bars 13, and the associated communication between proximal 11 and distal 12 nitinol springs, the middle area of graft 15 may twist or bunch and collapse, thereby shrinking or eliminating the passage for blood flow. Furthermore, the connecting bars 13 provide extra security during the deployment and positioning of graft 15. For example, if distal nitinol spring 12 is against a weak portion of the blood vessel wall and proximal nitinol spring 11 is against a strong portion, then the connecting bars 13 will help to stabilize distal nitinol spring 12.

Figure 1A:
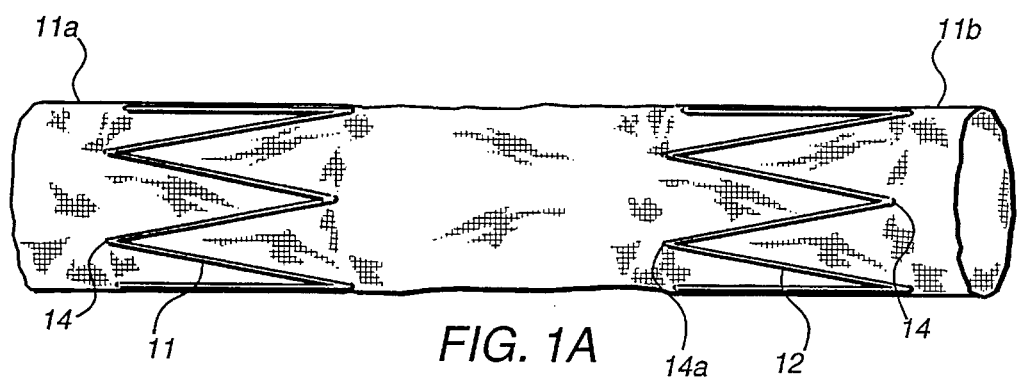

As shown in further FIG. 1a, in its most preferred embodiment, graft 15 contains cut away web portions wherein the material covering distal 12 an proximal 11 springs is cut away within the V portions to enhance flexibility in sizing.

Figure 2:
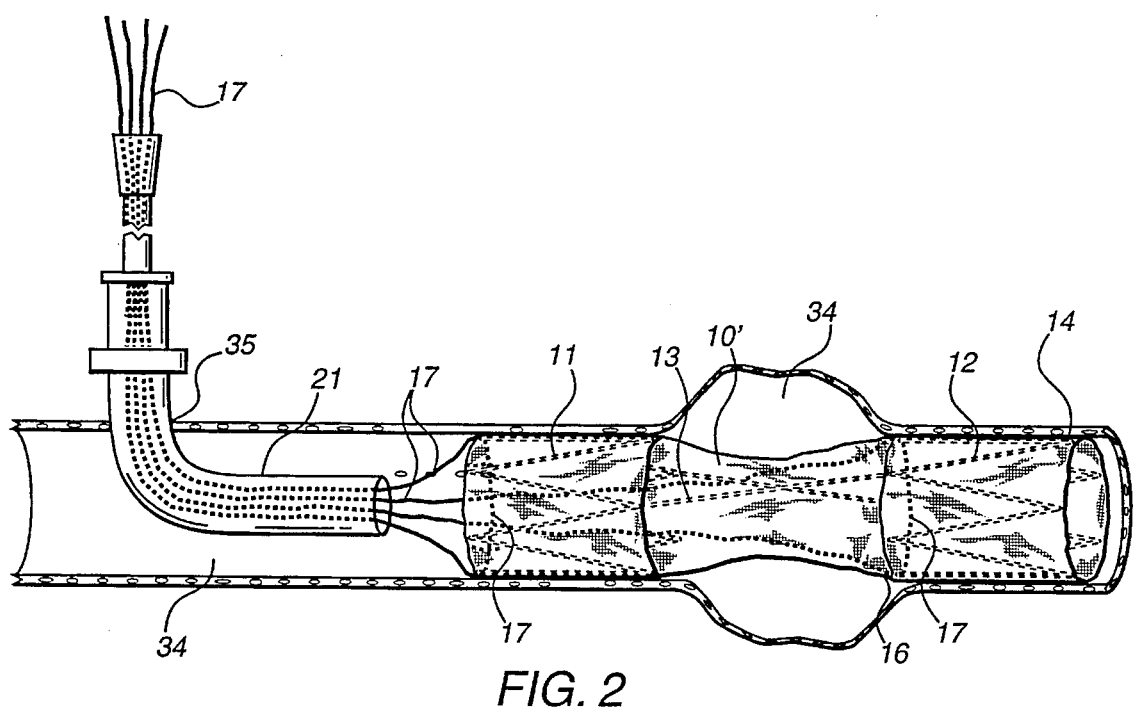
FIG. 2 is a side elevational view of a preferred embodiment of a graft within a ruptured blood vessel with a view of the nitinol springs, connecting bars, nitinol mesh extensions and the smaller, nondistensible middle portion, and the strings of the Taheri string system.

As shown in FIG. 2 in its most preferred embodiment, the middle portion 10' of graft 15 is smaller in diameter when graft 15 is deployed in the lumen of a blood vessel 34, than both end portions. This smaller diameter middle portion 10' provides greater flexibility in sizing than would a graft 15 having a middle portion 10' of equal or greater maximum diameter to the end portions. For example, if the full diameter of both end portions is equal to the full diameter of the middle portion 10' of graft 15, and if graft 15 is inserted into a blood vessel 34 of smaller diameter than of the middle 10' and end portions of graft 15, proximal 11 and distal 12 springs of the end portions would sufficiently compensate by expanding only to a diameter size consistent with the diameter of the lumen of the blood vessel 34. The middle portion 10', however, does not contain springs. It, therefore, would not have the sizing flexibility of the end portions and would be too large. Wrinkling or bunching of the material covering the middle portion 10' could result. This result could, again, substantially impair blood flow through graft 15, and may cause clotting. A graft 15 containing a smaller diameter middle portion 10' allows graft 15 to fit within a blood vessel 34 of equal or greater diameter than the middle portion 10' as long as the diameter of the blood vessel 34 is not in excess of that of the fully expanded end portions.

Figure 3:
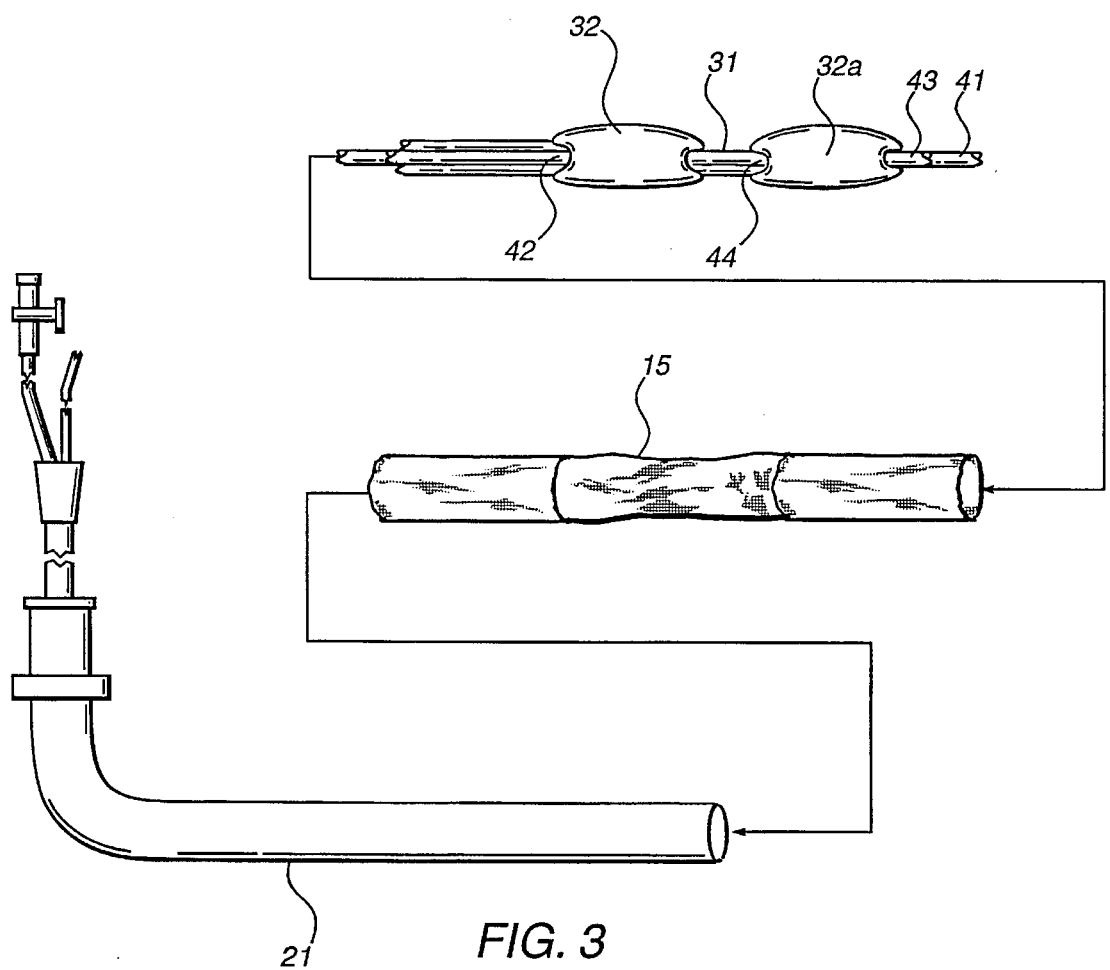
FIG. 3 is a side elevational view of a graft and insertion catheter, pre-loaded within a sheath.

As shown in FIG. 3, insertion catheter 31 with balloon 32 are pre-loaded within graft 15, prior to its introduction into blood vessel 34. Graft 15 is then compressed and loaded within sheath introducer 21, preferably a teflon sheath introducer 21, for delivery to the damaged region of blood vessel 34. An inflatable and deflatable graft balloon 32 and an inflatable and deflatable tip balloon 32a, preferably polyurethane balloons, are disposed about and integral with the distal end of insertion catheter 31. Sheath introducer 21 may also be comprised of material such as polyurethane, silicone, polyethylene, or other similar materials.

Figure 3A:
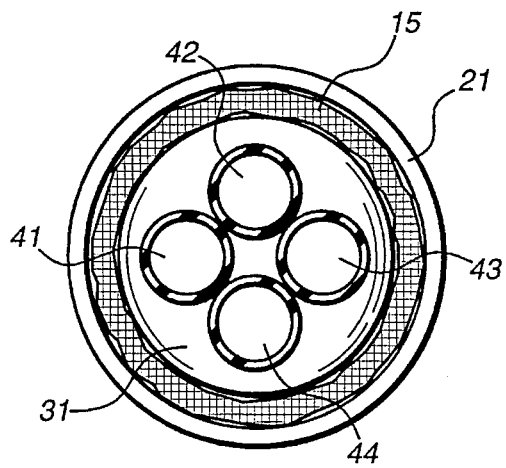
FIG. 3a is a cross sectional view of a graft and insertion catheter, pre-loaded within a sheath introducer.
Figure 3B:
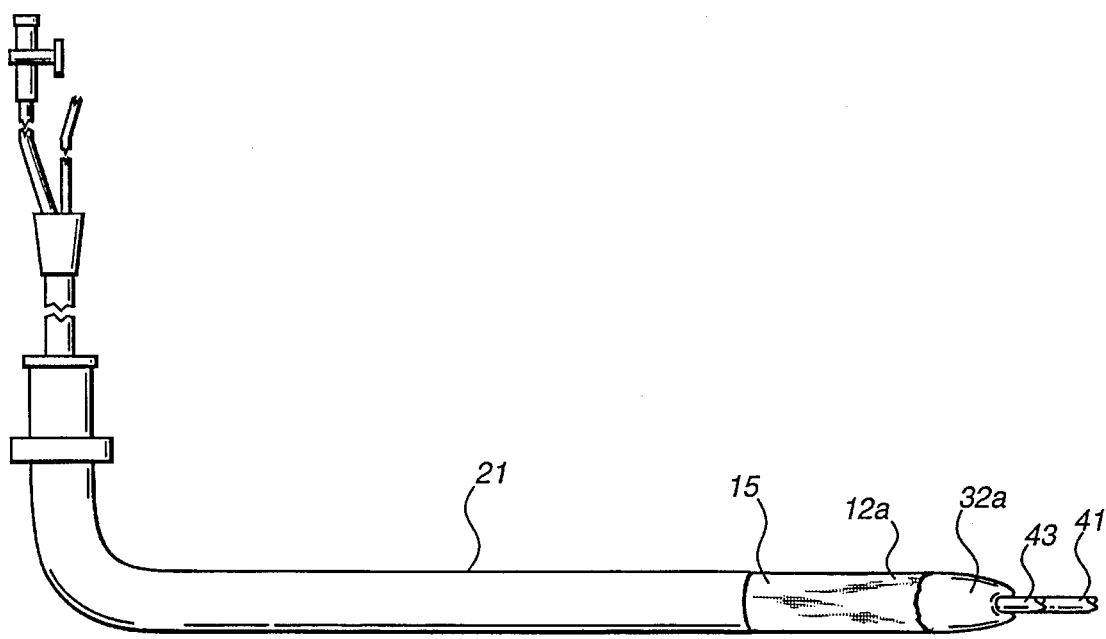
FIG. 3b is a side elevational view of the sheath introducer pre-loaded with graft and insertion catheter, with tip balloon of insertion catheter in the inflated position.

As shown in FIG. 3a, sheath introducer 21, after pre-loading, is disposed radially about, but not affixed to graft 15, and graft 15 is disposed radially about but not affixed to insertion catheter 31. As shown in FIG. 3b, after pre-loading, the portion of the insertion catheter having the tip balloon 32a extends outward from graft 15 and the distal end of sheath introducer 21. Tip balloon 32a is inflated as the pre-loaded sheath introducer is passed into and through the blood vessel 34 toward the rupture site for the purpose of provoking advanced dilation of blood vessel 34.

As shown further in FIG. 3, sheath introducer 21, is most preferably equipped with a homeostasis valve 22 and a side port 23. The homeostasis valve 22, most preferably comprised of latex, grips around the surface of insertion catheter 31 to prevent blood from leaking out of the patient at the entry site 35. The side port 23 provides a means for injecting contrast media into the blood vessel 34. Insertion catheter 31 is preferably comprised of a length sufficient to extend into the blood vessel beyond the site of rupture, while having a length sufficient at the proximal end for manipulation by the operator.

As shown further in FIG. 3, insertion catheter 31 is further comprised of four inner tracks; track one 41 having an opening at the distal end and all three tracks having an opening at proximal end of insertion catheter 31. Track one 41 is utilized in conjunction with a guide wire to guide insertion catheter 31 through blood vessel 34. Track one is further utilized for injection of contrast media or other fluid into blood vessel 34 to enhance visual communication with graft 15. Moreover, track two 42 opens into, and therefore communicates with graft balloon 32 of insertion catheter 31 to allow for injection of fluid, gaseous or liquid, from the opening at the proximal end. Additionally, track three 43, while having an opening at the proximal end, is closed at the distal end. Track three 43 is preferably used to facilitate the use of a condensing spring push rod for application of force to graft 15 during deployment of graft 15 into the lumen of blood vessel 34. The condensing spring push rod is flexible to enable it to maneuver through blood vessel 34 and most preferably contains a plunger at its tip to prevent outflow of blood through sheath introducer 21. Track four 44 opens into and therefore communicates with tip balloon 32a to allow for injection of a fluid, preferably a contrast media, into tip balloon 32a from the opening at proximal end of insertion catheter 31. Insertion catheter also most preferably contains an embedded kink resistant nitinol core wire and a conical shaped tip at its distal end.

Figure 4:
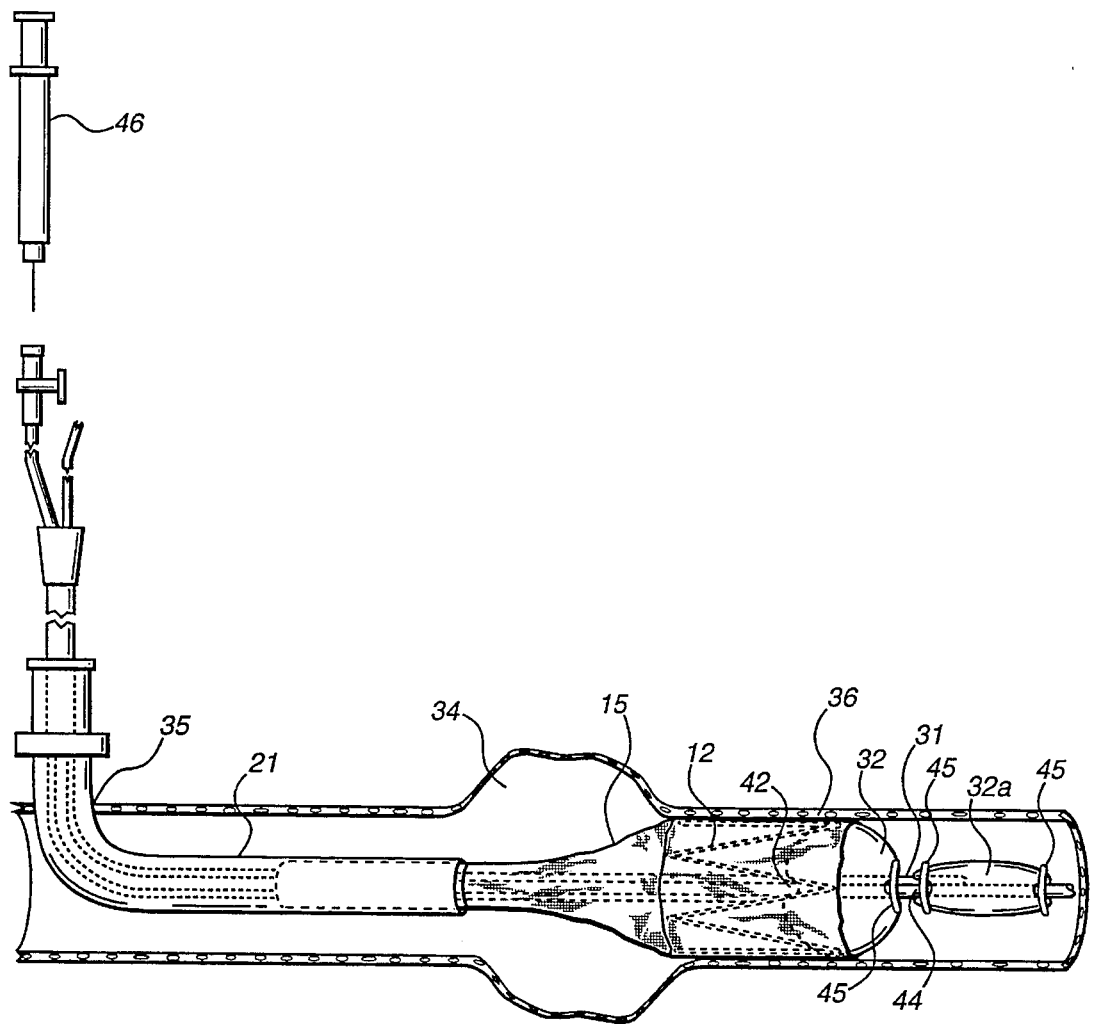
FIG. 4 is a side elevational view of a blood vessel containing the expanded distal nitinol spring and distal nitinol mesh extensions with the inflated graft balloon of the insertion catheter positioned therein with a metal ring positioned therebeside, as well as the sheath covering the proximal nitinol spring.

As shown in FIG. 4, insertion catheter 31 contains a balloon control means for inflation and deflation of graft balloon 32 and tip balloon 32a. The preferred means for inflating balloons 32 and 32a is by injecting a fluid, preferably a radiopaque dye, into balloons 32 and 32a with a syringe 46 through track two 42 and track four 44 of insertion catheter 31. The radiopaque dye provides not only for the inflation of balloons 32 and 32a, but also provides for visual communication with balloons 32 and 32a, thereby enabling the user to determine the location of balloons 32 and 32a relative to positions within graft 15.

As shown further in FIG. 4, for an alternative means of creating such visual communication a metal ring 45 may be positioned around insertion catheter 31 on either or both sides of graft balloon 32 and tip balloon 32a. The metal ring 45 would, thereby, replace the need for a radiopaque dye within balloon 32, thus allowing for the use of another fluid for inflation and deflation of balloons 32, 32a.

As shown further in FIG. 4, balloon 32 is inflatable to a size consistent with an ability to provide force against the interior of distal nitinol spring 12 during its expansion, after its release from sheath introducer 21, thereby providing additional support to distal nitinol spring 12 during placement of graft 15 within blood vessel 34 and removal of sheath introducer 21 from its position about graft 15. Furthermore, as also shown in FIG. 4, balloon 32 is inflatable to a size consistent with an ability to, at the same time, block blood flow through graft 15 during placement of graft 15.

Figure 5:
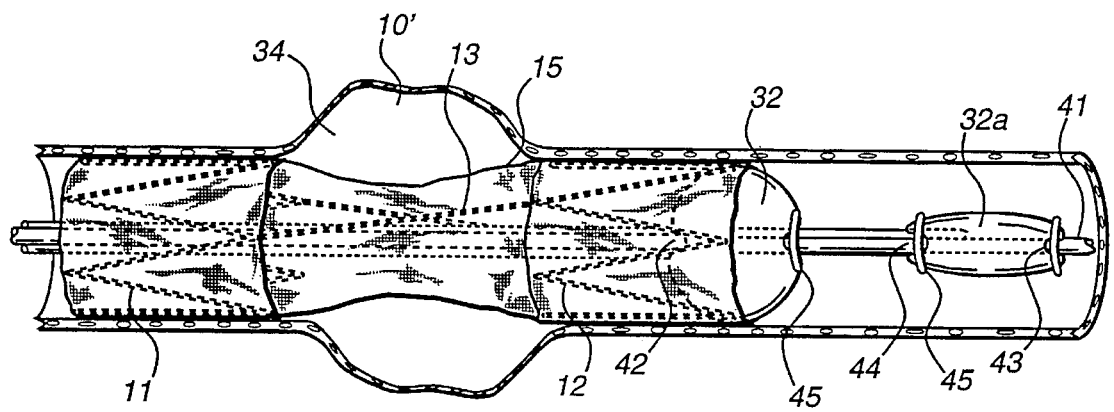
FIG. 5 is a side elevational view of a blood vessel containing a graft with expanded proximal and distal nitinol springs and nitinol mesh extensions, and an inflated graft balloon therein.

Moreover, as shown in FIG. 5, balloon 32 is inflatable for a duration consistent with the time period necessary to support distal nitinol spring 12 after it is released from sheath introducer 21 and particularly while proximal nitinol spring 11 is being released therefrom. Additionally, balloon 32 is inflatable for a duration consistent with the time period necessary to verify that graft 15 is secured in the appropriate position within and against the lumen wall; a time-period of at least 5 seconds.

Figure 5A:
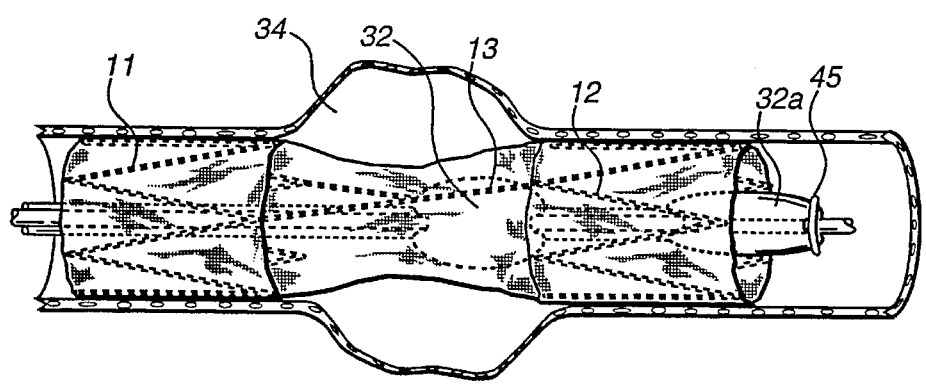
FIG. 5a is a side elevational view of a blood vessel containing a graft with expanded proximal and distal nitinol springs and nitinol mesh extensions, and a partially deflated graft balloon therein.

As shown in FIG. 5a, balloon 32 is also deflatable and inflatable to a size consistent with an ability to pass through graft 15 after complete placement of graft 15 within the lumen of blood vessel 34, and thereby provide the means for unraveling and fully opening graft 15, and for smoothing out wrinkles and twists that may be present in graft 15 after placement. As shown further in FIG. 5a, when balloon 32 is in the deflated position, insertion catheter 31 is movable within the length of graft 15 while at least partially deflated, for smoothing out any wrinkles and twists formed during the placement.

As shown further in FIG. 4, once graft 15 and sheath introducer 21 are positioned appropriately within the lumen of the blood vessel 34, sheath introducer 21 is slowly and gently pulled back across the length of graft 15 toward the point of entry 35 until it is removed from the lumen of the blood vessel 34. The sheath action of moving sheath introducer 21 toward the point of entry 35 causes distal nitinol spring 12 of graft 15 to be released and therefore, expanded into the lumen of the blood vessel 34. As shown further in FIG. 4, as distal nitinol spring 12 is deployed, balloon 32 of insertion catheter 31, pre-loaded within graft 15, is inflated in the center of distal nitinol spring 12 to support insertion catheter 31 in its connection to graft 15 so that force applied to nitinol core wire, condensing spring push rod, and insertion catheter 31 will communicate with graft 15 and aid in the release of graft 15 from sheath introducer 21. Furthermore, balloon 32 to provide extra strength to the friction fit of distal nitinol spring 12 against blood vessel wall 36 after distal spring 12 is released from sheath introducer 21. Balloon 32 is then used to determine whether distal nitinol spring 12 is positioned against a strong portion of the blood vessel wall 36. For example, if balloon 32 inflates without a sudden increase in resistance at a pre-determined point representing the pre-determined size, it is an indication that distal nitinol spring 12 is not deployed in the correct position, in that it is likely positioned within and against the ruptured portion of the blood vessel, and must be moved. If balloon 32 meets sudden, and appropriate resistance, this is an indication that graft 15 is placed with its distal nitinol spring 12 against a strong portion of the blood vessel wall 36.

As shown further in FIG. 4, the preferred inflation and deflation means for balloons 32, a syringe 46, is equipped with a means for measuring the amount of fluid injected into balloon 32 and a pressure gauge. As each unit of fluid is injected into balloon 32 and as balloon 32 inflates, pressure gauge will indicate steady resistance associated with the inflation of said balloon 32. When balloon 32 inflates to a size consistent with the diameter of the lumen of the blood vessel 34 and therefore, makes contact with the blood vessel wall 36, the resistance to further inflation of balloon 32 will suddenly increase. The sudden increase in resistance will be shown by an attached pressure gauge and represent graft's 15 contact with the blood vessel wall 36. The operator may then continue to pull sheath introducer 21 across the length of graft 15 toward the point of entry 35 and at the same time apply force to the nitinol core wire, condensing spring push rod, and insertion catheter 31. As shown further in FIG. 5, this sheath pulling action and force to graft 15 causes the release of proximal nitinol spring 11, thereby enabling its expansion within the lumen of the blood vessel 34. Balloon 32 may remain inflated to maintain communication of such force to graft 15 and support the position of graft 15 until after sheath introducer 21 releases proximal nitinol spring 11. As sheath introducer 21 is moved across proximal nitinol spring 11, thus releasing proximal nitinol spring 11, the additional resistance provided by balloon 32 secures distal nitinol spring 12 in its original placement position.

As shown further in FIG. 5a, after placement is complete, balloon 32 may be deflated slowly to gently introduce blood flow through graft 15 thereby preventing displacement of graft 15 which might be caused by a sudden rush of blood. The partially deflated balloon 32 may be moved throughout the length of graft 15 to unravel and fully open graft 15, and further to smooth out any wrinkles that may have formed in graft 15 during placement. Insertion catheter 31 may then be removed and if graft is appropriately positioned, incisions may be closed.

As shown further in FIG. 2, when graft 15 is fully deployed within the lumen of the blood vessel 34, the outer V portions 14 of both springs exert significant force against the blood vessel wall 36. Between 240 and 340 grams of force is exerted at that point to prevent leakage of blood to the outside of graft 15 between graft 15 exterior and the wall of the blood vessel 36, so as to prevent disruption of graft 15 placement. This will allow for a period of time to pass prior to stapling graft 15 to the blood vessel wall 36. Such stapling will permanently prevent such leakage and the growth of the rupture.

As shown further in FIG. 2, a string system may be used to partially collapse proximal nitinol spring 11 or distal nitinol spring 12, or both after sheath introducer 21 has been removed and graft 15 has been placed. The string system will facilitate repositioning graft 15 if graft 15 has been misplaced. The most preferred means for partially collapsing graft 15 for such repositioning is to utilize a string system which is comprised of two or more strings 17 pre-loaded in a position looped around two or preferably all of the outer V-shaped portions 14 of proximal nitinol spring 11 or inner V-portions 14a of distal nitinol spring 12, or most preferably both. Strings 17 must be of a length sufficient to reach from outside the body at the point of entry 35 and through the blood vessel 34 to the position of distal nitinol spring 12 after initial placement so as to allow for manipulation by the operator. If movement is required after placement, it may be effected by pulling strings 17 until the proximal 11 or distal 12 or both proximal 11 and distal 12 springs have partially or fully collapsed. Graft 15 may then be pulled by such strings 17 within the lumen of the blood vessel 34 to a more appropriate position therewithin or be pulled completely from the lumen of the blood vessel 34 out through the initial point of entry 35, then re-inserted. Strings 17, therefore, must be of a sufficient strength to collapse proximal 11 and distal 12 nitinol springs, and pull graft 15 through the blood vessel 34. When the operator is satisfied with the new position of graft 15 within the lumen of the blood vessel 34 he may pull one side of each string 17 until strings 17 are completely removed from the blood vessel 34.

Once distal 12 and proximal 11 nitinol springs have been released and proper placement of graft 15 is made, graft 15 may be permanently secured by means of an intravascular stapling system such as that disclosed in U.S. Pat. No. 4,872,874 to Taheri. It is most preferred to utilize a stapling system to add more permanency to the placement of graft 15 after a sufficient period of time has elapsed and it is determined that no further movement of graft 15 is required. Furthermore, the stapling will aid in the prevention of further expansion of the rupture site, and prevention of leakage of blood between graft 15 and blood vessel wall 36.

Figure 7:
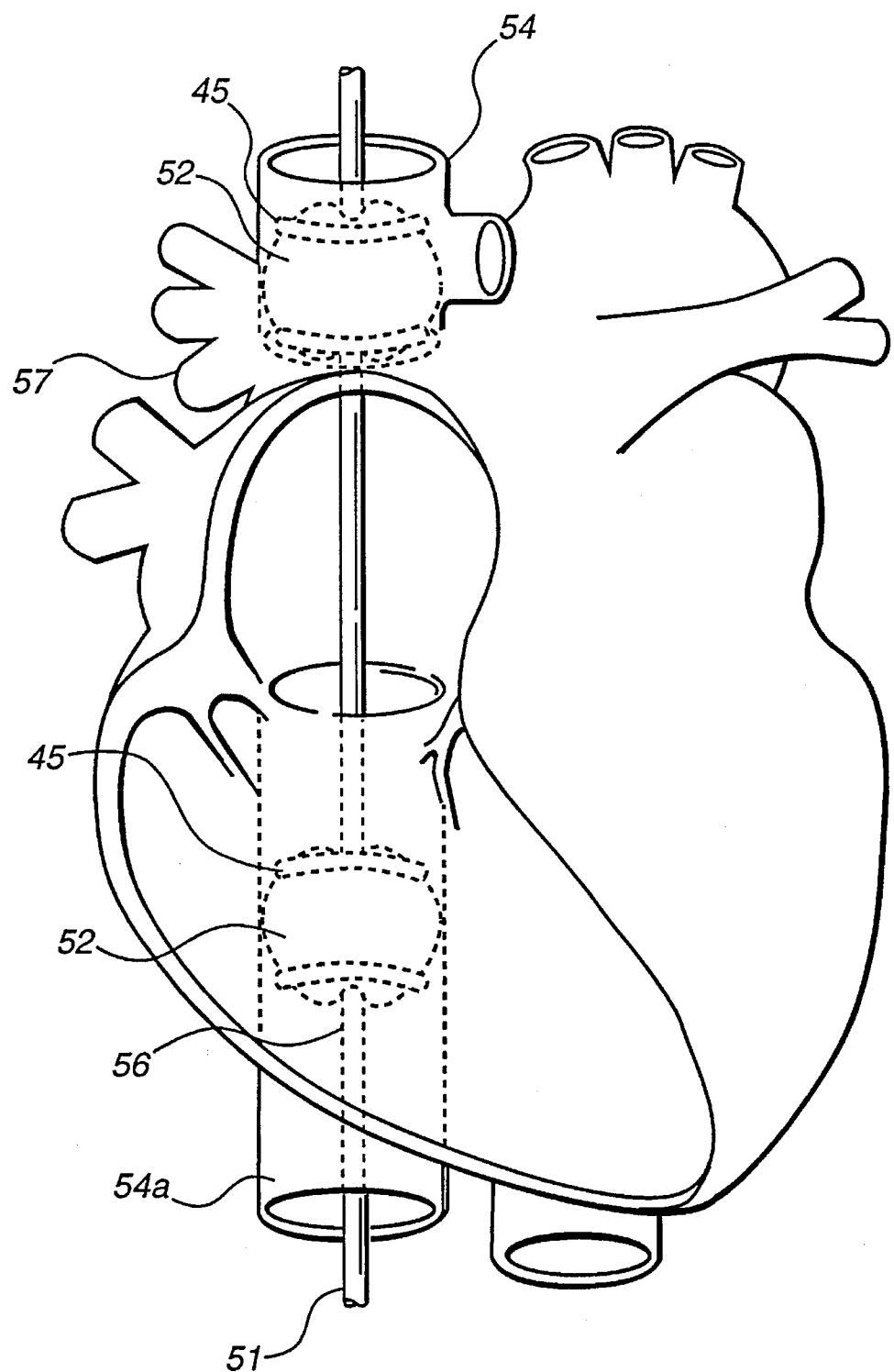
FIG. 7 is a side elevational view of a double balloon blocking catheter in the inferior and superior vena cava.

As shown in FIG. 7, another means for slowing or stopping blood flow during placement of graft 15, comprises the use of a double balloon blocking catheter 51 containing two inflatable and deflatable balloons 52 spaced sufficiently along the length of double balloon blocking catheter 51 to, when inflated and positioned appropriately, partially or fully block the blood flow into the right atrium at the points of entry associated with the superior 54 and inferior vena cava 54a. As with insertion catheter 31, double balloon blocking catheter 51 preferably contains a plurality of interior tracks. Track one 55 provides a means for utilizing a guide wire; and tracks two 56 and three 57 provide a pathway for fluid injection for inflation and deflation of balloons 52. Double balloon blocking catheter 51 is most preferably inserted into the jugular vein prior to or contemporaneous with the entry of the pre-loaded insertion catheter 31. Double balloon blocking catheter 51 is then passed through the superior vena cava 54 and into the inferior vena cava 54a.

As shown further in FIG. 7, metal rings 45 may be, again, placed on each side of the balloons 52 of double balloon blocking catheter 51 to enhance visual communication for positioning of balloons 52 at each point of entry into the right atrium 53. Furthermore, a radiopaque dye may be used as the fluid for inflation and deflation of balloons 52 to further enhance visual communication.

After double balloon blocking catheter 51 is positioned as described hereinabove, and sheath introducer 21 is positioned for placement of graft 15 as also described hereinabove, balloons 52 of blocking catheter 51 may be inflated to partially or fully block the blood flow into the right atrium while graft 15 is released from the sheath introducer 21 and placed appropriately within the blood vessel 34. Such inflation is preferably effected with a syringe. During inflation of balloons 52 of blocking catheter 51, blood flow must be monitored to determine the point when blood flow has ceased or slowed to an acceptable rate for placement of graft 15. It is most preferred to reduce the mean arterial pressure from normal which is 85–95 mm Hg to 30 mm Hg, and to reduce the pulmonary artery blood pressure from a normal which is 35 mm Hg to 5 mm Hg. After placement of graft 15, balloons 52 of blocking catheter 51 may be slowly deflated so as to gently reintroduce blood flow through the body. Such gentle reintroduction of blood flow will prevent dislodging graft 15 from a sudden rush of blood. Furthermore, blocking catheter 51 may be used in conjunction with balloon 32 of insertion catheter 31 for introduction of blood flow through graft 15.

Figure 8:
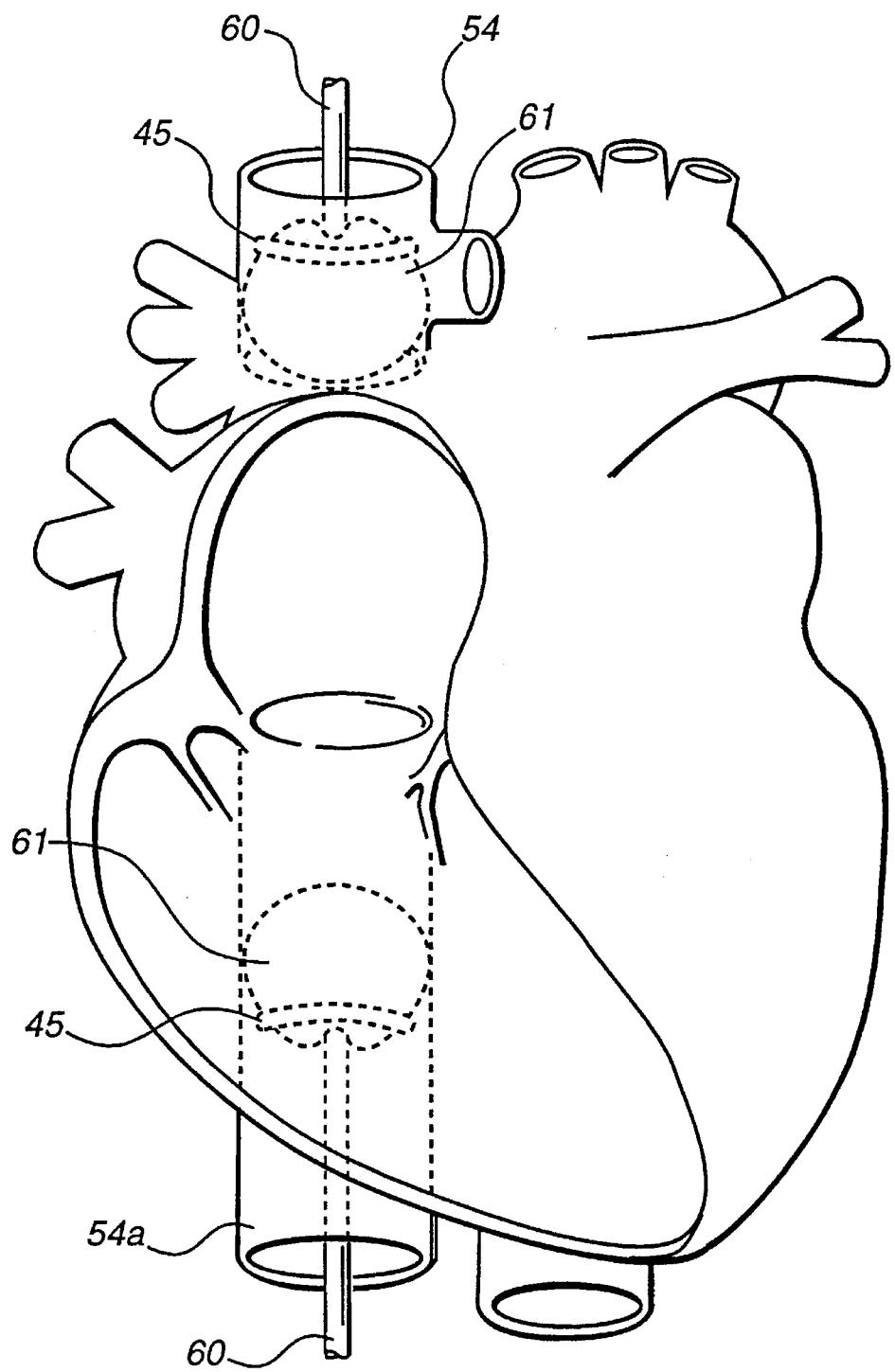
FIG. 8 is a side elevational view of two single balloon blocking catheters positioned in the superior and inferior vena cava.

As shown in FIG. 8, another means for slowing or stopping blood flow during placement of graft 15 comprises two single balloon blocking catheters 60, each containing one balloon 61 disposed about its distal end, and in fluid communication with an interior track of blocking catheter 62. Each single balloon blocking catheter 60, as with the double balloon blocking catheter 51 and insertion catheter 31, contains one or more interior tracks for the guide wire or core wire and the fluid injection into balloon 61. The single balloon blocking catheters 60, however, must be inserted separately into the superior vena cava 54 and inferior vena cava 54a, then passed through the respective veins until the balloon of each is positioned at its respective point of entry into the right atrium. The same blocking method is performed as described hereinabove.

Figure 6:
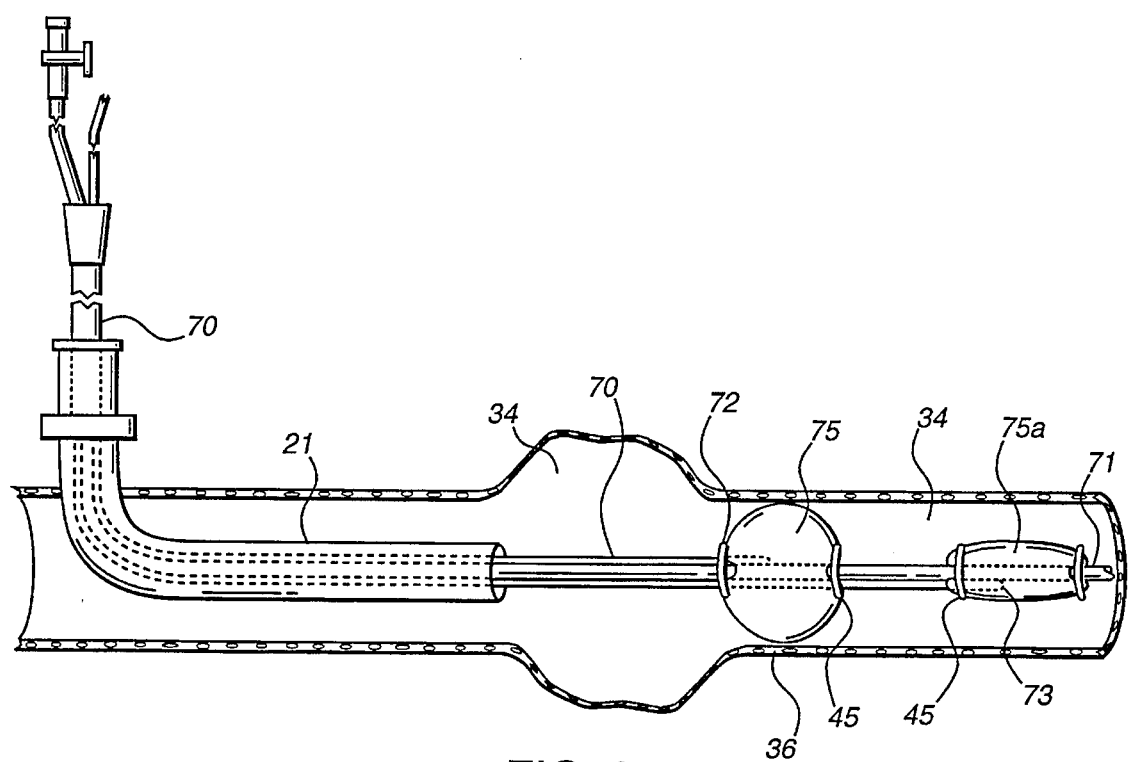
FIG. 6 is a side elevational view of a sizing catheter, its multiple interior tracks, and metal rings disposed about the distal portion near sizing balloon and tip balloon.

With regard to sizing graft 15 prior to insertion and placement, as shown in FIG. 6, a sizing catheter 70 is used to size the diameter of the lumen of the blood vessel 34 prior to selection of the appropriate graft 15. As shown further in FIG. 6, a sizing catheter 70 is comprised of a plurality of interior tracks each running along the length of sizing catheter 70, preferably four interior tracks, a sizing balloon 75 and a tip balloon 75a, each disposed about and integral with its distal end. All four tracks of the sizing catheter 70 have openings at the proximal end. Track one 71 of the sizing catheter 70 has an opening at the distal end and thereby provides an unobstructed pathway for injection of fluid through the sizing catheter 70 into the lumen of the blood vessel 34. Track two 72 of the sizing catheter 70, at its distal end, opens into sizing balloon 75 of the sizing catheter 70. Track three 73 of sizing catheter 70 opens into tip balloon 75a to facilitate inflation and deflation thereof.

Track one 71 of sizing catheter 70 is preferably utilized as a pathway for injection of contrast media into the blood vessel so as to enhance the visual communication with the sizing catheter 70 in its location within the blood vessel 34. Such injection is preferably effected with the use of a syringe at the proximal opening of the sizing catheter 70. As shown further in FIG. 6, a metal ring 45 may be placed around the sizing catheter 70 at a point on either or both sides of balloons 75 and 75a to further enhance visual communication. Track one 71 is further utilized for movement of sizing catheter along a previously placed guide wire through blood vessel 34.

Track two 72 of sizing catheter 70 is preferably utilized as a pathway for injection of fluid, preferably contrast media such as a radiopaque dye, into balloon 75 of sizing catheter 70 for inflation and deflation of balloon 75. Again, it is preferable to use a syringe for injection of the fluid. The injection means is preferably equipped with a means for measuring the amount of fluid injected into balloon 75 of sizing catheter 70.

As shown in FIG. 9, the infused volume multiplied by 1.50 equals balloon diameter and vessel diameter. The injection means is preferably equipped with a pressure gauge. As a balloon inflates, the resistance to such inflation remains constant until balloon 75 inflates to a size consistent with the diameter of the lumen of the blood vessel 34 and makes contact with the blood vessel wall 36. When such contact occurs between balloon 75 and the blood vessel wall 36, the pressure gauge will indicate a sudden increase in resistance to further inflation. At the point the pressure gauge indicates a sudden increase in resistance, a measurement of the amount of fluid injected will indicate the diameter of balloon 75, and therefore, the diameter of the lumen of the blood vessel 34.

The most preferred method of utilizing the sizing catheter 70 for sizing of a blood vessel 34 is to first place the sizing balloon 75 of the sizing catheter 70 at a position proximate to the site of the aneurysm. This can be determined by injecting a small amount of the radiopaque dye into balloon 75 or by obtaining visual communication utilizing metal rings 45 on either or both sides of balloon 75. Second, the operator, by utilizing the visual communication provided by the radiopaque dye or metal rings 45 must determine the location of the sizing balloon 75 in relation to the site of the aneurysm. When the sizing balloon 75 is positioned on the proximate side of the aneurysm, balloon 75 may be inflated until a sudden pressure increase from increased resistance is indicated by the pressure gauge. At the movement of sudden pressure increase, the operator must record the amount of fluid so injected, and convert that number to the increased diameter of balloon 75. The operator must then deflate balloon, advance the catheter 2 cms forward, and repeat procedure. Depth marks on the catheter surface may be used to verify depth position. The rupture site is easily identified by this sizing method during balloon 75 inflation. After one measurement is complete, the point of increased resistance is predictable. When sizing catheter 70 moves into the ruptured areas, balloon inflation will continue well beyond the predicted size. This, therefore, indicates to the operator that the rupture site has been reached. The length of the rupture site is determined by utilizing the sizing catheter depth marks. Radiopaque image photos should be taken every 2 cms. Such measurements at each 2 cm interval will enable the operator to determine not only the diameter of the lumen of the blood vessel 34, but the length of the rupture as well. After the size of the diameter of the blood vessel lumen and the length of the rupture have been determined, an appropriate graft may be selected for insertion.

As shown in FIG. 10, a graft size is determined after sizing a blood vessel by multiplying the blood vessel size by 1.33 then rounding up to the nearest 2 mm size from the following; 10, 12, 14, 16, 18, 20, 22, 24, 26, 28, 30, 32.

What is claimed is:

1. An apparatus for engrafting a blood vessel comprising:

a hollow tubular graft of a preselected cross section having a proximal end, a distal end, and a middle portion; and said hollow tubular graft being capable of substantially deforming so as to conform to an interior surface of said blood vessel;

a compressible and expandable proximal spring perpendicularly located at said proximal end of said hollow tubular graft, and said proximal spring being capable of deforming so as to conform to the interior surface of said blood vessel; said proximal spring containing sufficient outward force to exert continuous force against and inner wall of said blood vessel; said proximal spring being comprised of nitinol;

a compressible and expandable distal spring perpendicularly located at said distal end of said hollow tubular graft, and said distal spring being capable of deforming so as to conform to the interior surface of said blood vessel; said distal spring containing sufficient outward force to exert continuous force against the inner wall of said blood vessel; said distal spring being comprised of nitinol;

at least one flexible connecting bars for maintaining physical communication between said proximal and distal springs; said at least one connecting bars being comprised of nitinol;

a graft material; said graft material encasing said proximal spring, said distal spring, and said at least one connecting bars; said graft material being distensible at said distal and said proximal ends to facilitate expansion of said proximal and distal springs.

2. An apparatus according to claim 1 further comprising:

a transport and deployment means for delivering said hollow tubular graft to an engrafting site of said blood vessel.

3. An apparatus according to claim 1 wherein said force exerted against the inner wall of said blood vessel by said proximal and distal nitinol springs is sufficient to prevent blood flow between said hollow tubular graft and the inner wall of said blood vessel.

4. An apparatus according to claim 1 wherein said force exerted against the inner wall of said blood vessel by said proximal and distal nitinol springs is between 240 grams and 340 grams.

5. An apparatus according to claim 1 wherein middle portion of said graft contains a smaller diameter than said distal and said proximal ends.

6. An apparatus according to claim 1 wherein said middle portion of said graft material is non-distensible.

7. An apparatus according to claim 1 further comprising a first nitinol mesh extension connected to said proximal nitinol spring; and a second nitinol mesh extension connected to said distal nitinol spring.

8. An apparatus according to claim 1 wherein said graft further comprises:

one or more outer v-shaped portions of said proximal nitinol spring, one or more strings having a first and second end; said one or more strings movably connected to said one or more outer v-shaped portions of said proximal nitinol spring.

9. An apparatus according to claim 2 wherein said transport and deployment means comprises:

an insertion catheter having a length, a proximal end, a distal end, and one or more inner tracks;

a first inner track having an opening at both said proximal and said distal ends;

a second inner track having an opening at said proximal end and being closed at said distal end;

a nitinol core wire embedded in and along said length of said insertion catheter;

a controllable inflatable and deflatable graft balloon disposed about and integral with said insertion catheter; a third inner track having a first opening at said proximal end and a second opening into said controllable inflatable and deflatable graft balloon;

a controllable inflatable and deflatable tip balloon disposed about and integral with said distal end of said insertion catheter;

a fourth inner track having a first opening at said proximal end of said insertion catheter and a second opening into said controllable inflatable and deflatable tip balloon;

a means for inflating and deflating said controllable inflatable and deflatable graft balloon and tip balloon; and a sheath introducer.

10. A method for engrafting a blood vessel comprising the steps of:

a. providing a sizing means for sizing a diameter of said blood vessel and the length of a rupture;

b. sizing said diameter of said blood vessel and length of said rupture with said sizing means;

c. pre-loading an insertion catheter having a tip balloon, a graft balloon, and at least one inner track within a graft having a distal and proximal end; positioning said insertion catheter with said tip balloon extending outward from said distal end of said graft;

d. pre-loading said graft and said insertion catheter within a sheath introducer;

e. providing a means for inflating and deflating said tip balloon;

f. inflating said tip balloon;

g. inserting said sheath introducer into said blood vessel;

h. moving said sheath introducer through said blood vessel to said rupture;

i. providing a means for verifying position of said graft;

j. verifying said position of said graft;

k. providing a means for inflating and deflating said graft balloon:

l. providing a push rod;

m. inserting said push rod into one of said one or more inner tracks of said insertion catheter;

n. providing a means for reducing a mean arterial and pulmonary artery venous blood pressure and subsequently returning said mean arterial pressure and pulmonary artery venous blood pressure to a normal pressure;

o. reducing said mean arterial and pulmonary artery venous blood pressure to said normal pressure;

p. inflating said graft balloon while applying inward force to said push rod and pulling back said sheath introducer until both said proximal and distal nitinol springs are released from said sheath introducer;

q. returning said mean arterial pressure and pulmonary artery venous blood pressure to said normal pressure;

r. slowly deflating said graft balloon;

s. removing said insertion catheter from said blood vessel.

11. A method according to claim 10 wherein said means for reducing a mean arterial and pulmonary artery venous blood pressure and subsequently returning said mean arterial and pulmonary artery venous blood pressure to a normal pressure is a double balloon blocking catheter.

12. A method according to claim 10 wherein said means for reducing a mean arterial and pulmonary artery venous blood pressure and subsequently returning said mean arterial and pulmonary artery venous blood pressure to a normal pressure are two single balloon blocking catheters.

13. A method according to claim 10 wherein said means for verifying the position of said graft is injecting contrast media into a blood vessel lumen.

14. A method according to claim 10 wherein said means for inflating and deflating said graft balloon is a syringe.

* * * * *